(12) United States Patent
Rosinko et al.

(10) Patent No.: US 10,780,215 B2
(45) Date of Patent: *Sep. 22, 2020

(54) DEVICE AND METHOD FOR SETTING THERAPEUTIC PARAMETERS FOR AN INFUSION DEVICE

(71) Applicant: Tandem Diabetes Care, Inc., San Diego, CA (US)

(72) Inventors: Mike Rosinko, Anaheim, CA (US); Phil Lamb, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 806 days.

This patent is subject to a terminal disclaimer.

(21) Appl. No.: 15/470,191

(22) Filed: Mar. 27, 2017

(65) Prior Publication Data

US 2017/0246380 A1    Aug. 31, 2017

Related U.S. Application Data

(63) Continuation of application No. 13/832,841, filed on Mar. 15, 2013, now Pat. No. 9,603,995.

(51) Int. Cl.
*A61M 5/142* (2006.01)
*A61M 5/14* (2006.01)
*A61M 5/168* (2006.01)

(52) U.S. Cl.
CPC .... *A61M 5/14244* (2013.01); *A61M 5/14216* (2013.01); *A61M 5/1413* (2013.01);
(Continued)

(58) Field of Classification Search
CPC ...... A61M 2005/14268; A61M 5/1413; A61M 2209/045; A61M 2005/14573;
(Continued)

(56) References Cited

U.S. PATENT DOCUMENTS

| 2,398,234 A | 4/1946 | Long |
| 4,445,885 A | 5/1984 | Kifune |

(Continued)

FOREIGN PATENT DOCUMENTS

| EP | 2410448 | 1/2012 |
| JP | 2012187365 | 10/2012 |

(Continued)

OTHER PUBLICATIONS

US 8,333,733 B2, 12/2012, Lanigan et al. (withdrawn)
(Continued)

*Primary Examiner* — Scott J Medway
(74) *Attorney, Agent, or Firm* — Patterson Thuente Pedersen, P.A.

(57) ABSTRACT

Embodiments are directed to infusion devices, systems, and methods to detect a capacity of a collapsible fluid reservoir of an infusion cartridge and/or a volume of a fluid disposed in the collapsible fluid reservoir or some other parameters of the infusion cartridge, and setting corresponding therapeutic parameters of an infusion device. Embodiments may include, obtaining data on the volume of fluid in the collapsible fluid reservoir, analyzing the obtained data to determine the setting of therapeutic parameters, and setting one or more therapeutic parameters of an infusion device.

32 Claims, 12 Drawing Sheets

(52) U.S. Cl.
CPC . *A61M 5/1684* (2013.01); *A61M 2005/14268* (2013.01); *A61M 2205/3306* (2013.01); *A61M 2205/3331* (2013.01); *A61M 2205/3351* (2013.01); *A61M 2205/3389* (2013.01); *A61M 2205/50* (2013.01); *A61M 2205/502* (2013.01); *A61M 2205/6018* (2013.01); *A61M 2205/6036* (2013.01); *A61M 2205/6054* (2013.01); *A61M 2205/6072* (2013.01)

(58) Field of Classification Search
CPC ...... A61M 2205/18; A61M 2205/3561; A61M 2205/3569; A61M 2205/3584; A61M 2205/3592; A61M 2205/502; A61M 2205/581; A61M 2205/582; A61M 2205/583
See application file for complete search history.

(56) References Cited

U.S. PATENT DOCUMENTS

| | | |
|---|---|---|
| 4,741,736 A | 5/1988 | Brown |
| 5,085,644 A | 2/1992 | Watson et al. |
| 5,153,827 A | 10/1992 | Coutre et al. |
| 5,167,633 A | 12/1992 | Mann et al. |
| 5,176,644 A | 1/1993 | Srisathapat et al. |
| 5,186,431 A | 2/1993 | Tamari |
| 5,197,322 A | 3/1993 | Indravudh |
| 5,231,616 A | 7/1993 | Oliver et al. |
| 5,272,909 A | 12/1993 | Nguyen et al. |
| 5,279,585 A | 1/1994 | Balkwill |
| 5,279,586 A | 1/1994 | Balkwill |
| 5,290,684 A | 3/1994 | Kelly |
| 5,336,051 A | 8/1994 | Tamari |
| 5,368,555 A | 11/1994 | Sussman et al. |
| 5,389,078 A | 2/1995 | Zalesky et al. |
| 5,403,551 A | 4/1995 | Galloway et al. |
| 5,429,483 A | 7/1995 | Tamari |
| 5,438,510 A | 8/1995 | Bryant et al. |
| 5,442,950 A | 8/1995 | Unalmiser et al. |
| 5,443,450 A | 8/1995 | Kratoska et al. |
| 5,445,616 A | 8/1995 | Kratoska et al. |
| 5,460,945 A | 10/1995 | Springer et al. |
| 5,514,103 A | 5/1996 | Srisathapat et al. |
| 5,634,779 A | 6/1997 | Eysymontt |
| 5,634,896 A | 6/1997 | Bryant et al. |
| 5,730,149 A | 3/1998 | Nakayama et al. |
| 5,897,530 A | 4/1999 | Jackson |
| 5,957,890 A | 9/1999 | Mann et al. |
| 5,984,894 A | 11/1999 | Poulsen et al. |
| 6,001,585 A | 12/1999 | Gramer |
| 6,126,642 A | 10/2000 | Kriesel et al. |
| 6,152,898 A | 11/2000 | Olsen |
| 6,164,924 A | 12/2000 | Gruett et al. |
| 6,283,949 B1 | 9/2001 | Roorda |
| 6,319,245 B1 | 11/2001 | Berrigan |
| 6,423,035 B1 | 7/2002 | Das et al. |
| 6,458,102 B1 | 10/2002 | Mann et al. |
| 6,471,689 B1 | 10/2002 | Joseph et al. |
| 6,520,936 B1 | 2/2003 | Mann |
| 6,562,001 B2 | 5/2003 | Lebel et al. |
| 6,592,860 B1 | 7/2003 | Levy et al. |
| 6,652,510 B2 | 11/2003 | Lord et al. |
| 6,692,456 B1 | 2/2004 | Eppstein et al. |
| 6,740,059 B2 | 5/2004 | Flaherty |
| 6,746,438 B1 | 6/2004 | Arnissolle |
| 6,752,787 B1 | 6/2004 | Causey et al. |
| 6,790,198 B1 | 9/2004 | White et al. |
| 6,857,572 B2 | 2/2005 | Martin et al. |
| 6,928,338 B1 | 8/2005 | Buchser et al. |
| 6,951,553 B2 | 10/2005 | Bubb et al. |
| 6,981,967 B2 | 1/2006 | Massengale et al. |
| 7,029,455 B2 | 4/2006 | Flaherty |
| 7,066,922 B2 | 6/2006 | Angel |
| 7,107,706 B1 | 9/2006 | Bailey et al. |
| 7,137,964 B2 | 11/2006 | Flaherty |
| 7,186,236 B2 | 3/2007 | Gibson et al. |
| 7,201,730 B2 | 4/2007 | Davidner et al. |
| 7,207,964 B2 | 4/2007 | Davidner et al. |
| 7,306,578 B2 | 12/2007 | Gray et al. |
| 7,334,556 B2 | 2/2008 | Wachigai et al. |
| 7,338,464 B2 | 3/2008 | Blischak et al. |
| 7,341,577 B2 | 3/2008 | Gill |
| 7,344,507 B2 | 3/2008 | Briggs et al. |
| 7,351,239 B2 | 4/2008 | Gill |
| 7,364,568 B2 | 4/2008 | Angel et al. |
| 7,445,616 B2 | 11/2008 | Petrakis |
| 7,517,440 B2 | 4/2009 | Anex et al. |
| 7,563,255 B2 | 7/2009 | Adamis et al. |
| 7,657,297 B2 | 2/2010 | Simpson et al. |
| 7,678,762 B2 | 3/2010 | Green et al. |
| 7,678,763 B2 | 3/2010 | Green et al. |
| 7,683,029 B2 | 3/2010 | Hindle et al. |
| 7,713,574 B2 | 5/2010 | Brister et al. |
| 7,774,145 B2 | 8/2010 | Brauker et al. |
| 7,794,434 B2 | 9/2010 | Mounce et al. |
| 7,811,262 B2 | 10/2010 | Moberg et al. |
| 7,811,279 B2 | 10/2010 | John |
| 7,828,764 B2 | 11/2010 | Moberg et al. |
| 7,875,022 B2 | 1/2011 | Wenger et al. |
| 7,935,104 B2 | 5/2011 | Yodfat et al. |
| 7,935,105 B2 | 5/2011 | Miller et al. |
| 8,034,026 B2 | 10/2011 | Grant et al. |
| 8,037,226 B2 | 10/2011 | Miller et al. |
| 8,066,629 B2 | 11/2011 | Dlugos |
| 8,083,730 B2 | 12/2011 | Miesel |
| 8,105,265 B2 | 1/2012 | Demers et al. |
| 8,109,893 B2 | 2/2012 | Lande |
| 8,133,197 B2 | 3/2012 | Blomquist et al. |
| 8,117,739 B2 | 5/2012 | Cartledge et al. |
| 8,202,267 B2 | 6/2012 | Field et al. |
| 8,211,093 B2 | 7/2012 | Miller et al. |
| 8,285,328 B2 | 10/2012 | Caffey et al. |
| 8,287,495 B2 | 10/2012 | Michaud et al. |
| 8,298,184 B2 | 10/2012 | DiPerna et al. |
| 8,313,433 B2 | 11/2012 | Cohen |
| 8,382,703 B1 | 2/2013 | Abdelaal |
| 8,414,563 B2 | 4/2013 | Kamen et al. |
| 8,562,590 B2 | 10/2013 | Yodfat |
| 8,952,794 B2 | 2/2015 | Blomquist |
| 9,132,227 B2 | 9/2015 | Bryant, Jr. |
| 9,259,531 B2 | 2/2016 | Kamen |
| 9,603,995 B2 | 3/2017 | Rosinko et al. |
| 2001/0041869 A1 | 11/2001 | Causey et al. |
| 2002/0072733 A1 | 6/2002 | Flaherty |
| 2002/0169636 A1 | 11/2002 | Eggers et al. |
| 2002/0173769 A1 | 11/2002 | Gray et al. |
| 2003/0135388 A1 | 7/2003 | Martucci et al. |
| 2004/0172222 A1 | 9/2004 | Simpson et al. |
| 2004/0176984 A1 | 9/2004 | White et al. |
| 2005/0171512 A1 | 8/2005 | Flaherty |
| 2006/0031094 A1 | 2/2006 | Cohen et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051765 A1 | 2/2008 | Mounce |
| 2008/0097327 A1 | 4/2008 | Bente et al. |
| 2009/0069746 A1 | 3/2009 | Miller et al. |
| 2009/0069785 A1 | 3/2009 | Miller et al. |
| 2009/0118594 A1 | 5/2009 | Zdeblick |
| 2009/0156990 A1 | 6/2009 | Wenger et al. |
| 2009/0171324 A1 | 7/2009 | Chong et al. |
| 2009/0192724 A1 | 7/2009 | Brauker et al. |
| 2009/0254037 A1 | 10/2009 | Bryant, Jr. et al. |
| 2009/0275886 A1 | 11/2009 | Blomquist et al. |
| 2009/0292245 A1 | 11/2009 | Basso et al. |
| 2010/0010423 A1 | 1/2010 | Yu et al. |
| 2010/0010427 A1 | 1/2010 | Yu et al. |
| 2010/0121169 A1 | 5/2010 | Petisce et al. |
| 2010/0121306 A1 | 5/2010 | Yodfat et al. |

(56) References Cited

U.S. PATENT DOCUMENTS

| | | |
|---|---|---|
| 2010/0179402 A1 | 7/2010 | Goode, Jr. et al. |
| 2010/0198183 A1 | 8/2010 | Lanigan et al. |
| 2010/0214106 A1 | 8/2010 | Braun et al. |
| 2010/0218586 A1 | 9/2010 | Rosinko et al. |
| 2010/0249706 A1 | 9/2010 | Clemente |
| 2010/0262078 A1 | 10/2010 | Blomquist |
| 2011/0009823 A1 | 1/2011 | Chong et al. |
| 2011/0040247 A1 | 2/2011 | Mandro et al. |
| 2011/0046697 A1 | 2/2011 | Gerber et al. |
| 2011/0047499 A1 | 2/2011 | Mandro et al. |
| 2011/0054390 A1 | 3/2011 | Searle et al. |
| 2011/0060280 A1 | 3/2011 | Caffey et al. |
| 2011/0082439 A1 | 4/2011 | Wenger et al. |
| 2011/0092921 A1 | 4/2011 | Beling et al. |
| 2011/0093294 A1 | 4/2011 | Elahi et al. |
| 2011/0098635 A1 | 4/2011 | Helmore et al. |
| 2011/0107853 A1 | 5/2011 | Studer |
| 2011/0108158 A1 | 5/2011 | Huwiler et al. |
| 2011/0144586 A1 | 6/2011 | Michaud et al. |
| 2011/0144616 A1 | 6/2011 | Michaud et al. |
| 2011/0152756 A1 | 6/2011 | Drew |
| 2011/0152770 A1 | 6/2011 | DiPerna et al. |
| 2011/0152824 A1 | 6/2011 | DiPerna et al. |
| 2011/0166544 A1 | 7/2011 | Verhoef et al. |
| 2011/0190614 A1 | 8/2011 | Brister et al. |
| 2011/0190694 A1 | 8/2011 | Lanier et al. |
| 2011/0208123 A1 | 8/2011 | Gray et al. |
| 2011/0257895 A1 | 10/2011 | Brauker et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029468 A1 | 2/2012 | DiPerna et al. |
| 2012/0029708 A1 | 2/2012 | Miller et al. |
| 2012/0030610 A1 | 2/2012 | DiPerna et al. |
| 2012/0179130 A1 | 7/2012 | Barnes et al. |
| 2012/0232520 A1 | 9/2012 | Sloan et al. |
| 2013/0053816 A1 | 2/2013 | DiPerna et al. |
| 2013/0131630 A1 | 5/2013 | Blomquist |
| 2014/0039392 A1 | 2/2014 | Geipel et al. |
| 2014/0039455 A1 | 2/2014 | Miller |
| 2014/0054883 A1 | 2/2014 | Lanigan et al. |
| 2014/0276420 A1 | 9/2014 | Rosinko |
| 2014/0276531 A1 | 9/2014 | Walsh |
| 2014/0276556 A1 | 9/2014 | Saint et al. |
| 2014/0276569 A1 | 9/2014 | Kruse |
| 2014/0276574 A1 | 9/2014 | Saint |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0082188 A1 | 3/2016 | Blomquist et al. |

FOREIGN PATENT DOCUMENTS

| | | |
|---|---|---|
| WO | WO0040346 A1 | 7/2000 |
| WO | WO0072900 A1 | 12/2000 |
| WO | WO 03/017914 A1 | 3/2003 |
| WO | WO2010056663 | 5/2010 |
| WO | WO2010078084 | 7/2010 |
| WO | WO2012022771 | 2/2012 |

OTHER PUBLICATIONS

Communication dated Jan. 7, 2019 for EP Application No. 14767298. 4, pages.

Application and File History for U.S. Appl. No. 13/832,841, filed Mar. 15, 2013, inventors Rosinko et al.

European Search Report for European Application No. 14767298 dated Nov. 22, 2016.

International Search Report and Written Opinion dated Jun. 9, 2014 for International Application No. PCT/US2014/018705.

Communication dated Apr. 4, 2018 for EP Application No. 14767298. 4, 3 pages.

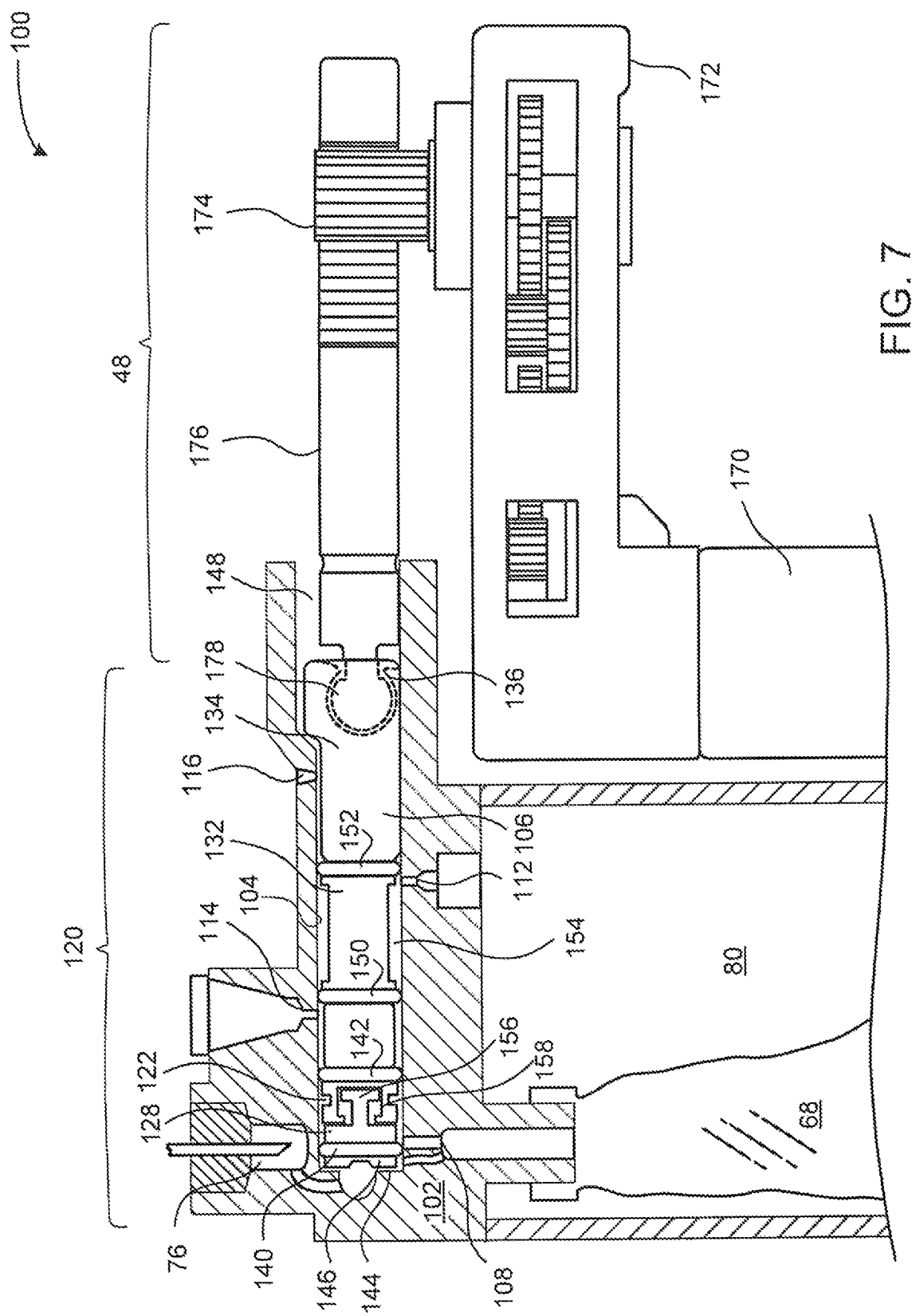

_DEVICE AND METHOD FOR SETTING THERAPEUTIC PARAMETERS FOR AN INFUSION DEVICE_

RELATED APPLICATION

This application is a continuation of application Ser. No. 13/832,841 filed Mar. 15, 2013, which is hereby fully incorporated herein by reference.

BACKGROUND

There are many applications in academic, industrial, and medical fields, as well as others, that benefit from devices and methods that are capable of accurately and controllably delivering fluids, including liquids and gases that have a beneficial effect when administered in known and controlled quantities. Such devices and methods are particularly useful in the medical field where treatments for many patients includes the administration of a known amount of a substance at predetermined intervals. As the number of commercially available delivery systems increase, different types of medication holding cartridges or infusion cartridges are made available.

Insulin-injecting pumps have been developed for the administration of insulin for those suffering from both type I and II diabetes. Continuous subcutaneous insulin injection and/or infusion therapy with portable infusion devices has been adapted for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

To discriminate between the large varieties of available cartridges, numerous coding schemes have been developed for recognizing the different types of cartridges in order that the delivery of a specific amount of a medicament is allowed by a delivery device. Generally, available systems are limited by the variety of coding schemes they can handle. Existing systems may also be limited by the scope of adjustments made, as a result of obtaining cartridge identification information Therefore, devices and methods capable of automatically and reliably recognizing a wide variety of cartridges, and implementing useful adjustments to the delivery systems are needed.

SUMMARY

Some embodiments include a method for detecting a capacity of a drug delivery reservoir of an infusion cartridge and setting therapeutic parameters of an infusion device setting based on the detected capacity. The method may include obtaining data on the capacity of the drug delivery reservoir, analyzing the obtained data on the capacity of the drug delivery reservoir, determining the setting of therapeutic parameters, and setting one or more therapeutic parameters of an infusion device based on the capacity data.

Some embodiments include a method for detecting a capacity of a collapsible fluid reservoir in an infusion cartridge and setting therapeutic parameters of an infusion device such as a portable or ambulatory infusion pump. The method can include obtaining data on the capacity of the collapsible fluid reservoir, analyzing obtained data on the capacity of the collapsible fluid reservoir to determine the setting of therapeutic parameters of the infusion device, and setting one or more therapeutic parameters of the infusion device. The therapeutic parameters can include a basal rate range, a bolus volume range, a max bolus volume range, and insulin sensitivity. Data on the capacity of the collapsible fluid reservoir can be obtained by reading optical indicia, reading signals from a radio frequency identification (RFID) tag or sensing positions of a plurality switches coupled to mechanical sensors of the infusion device that are registered with surface grooves on the infusion cartridge indicating.

Some embodiments include a method for detecting a volume of a fluid disposed in a collapsible fluid reservoir of an infusion cartridge and setting therapeutic parameters of an infusion device. The method includes obtaining data on the volume of the fluid disposed in a collapsible fluid reservoir; analyzing obtained data on the volume of the fluid to determine the setting of therapeutic parameters; and setting one or more therapeutic parameters of an infusion device. The therapeutic parameters can include a basal rate range, a bolus volume range, a max bolus volume range, and insulin sensitivity. Data on the volume of the fluid disposed in the collapsible fluid reservoir can be obtained by taking a plurality of pressure sensor readings, which are indicative of the volume of the fluid disposed in the collapsible fluid reservoir.

Some embodiments include an infusion device such as a portable infusion pump configured for detecting the capacity of a drug delivery reservoir or a volume of fluid disposed inside an infusion cartridge that may be attached to it, and for setting therapeutic parameters for the infusion device. The infusion cartridge may include a delivery mechanism for effectuating the delivery of fluid. The delivery mechanism may include an axial bore. A first and a second inlet port may be in fluid communication with an interior volume of the axial bore. The second inlet port may be axially spaced from the first inlet port. At least one outlet port, which may be axially spaced from the inlet ports, may also be in fluid communication with the interior volume of the axial bore. A spool may be disposed within the axial bore. The spool may be axially translatable within the axial bore and may form a constrained variable volume in conjunction with an interior surface of the axial bore. The infusion cartridge may also include a drug delivery reservoir for storing fluid. The drug delivery reservoir may include an interior volume that may be in fluid communication with the first inlet port. The infusion device may further include an infusion pump. The infusion pump may include a drive mechanism which may be operatively coupled to the spool. The infusion pump may be configured to impart controlled axial movement to the spool and may translate the constrained variable volume from the inlet ports to the outlet port. The infusion device may also include a processor. The processor may determine the capacity of the drug delivery reservoir or the volume of fluid disposed in the drug delivery reservoir and may set therapeutic parameters. The processor may be coupled to a memory and it may be configured for receiving input data from the memory. The processor may use the input data for generating therapeutic parameters for the infusion device. The memory may be configured for receiving, storing and communicating input data to the processor. A display may be coupled to the processer. The display may be configured for displaying a request to a user for input data. The display may be further configured for receiving user input data in response to the request and for display, communicating that data to the memory.

Certain embodiments are described further in the following description, examples, claims, and drawings. These features of embodiments will become more apparent from the following detailed description when taken in conjunction with the accompanying exemplary drawings.

BRIEF DESCRIPTION OF THE DRAWINGS

FIG. 7 is an elevation view in partial section of a delivery mechanism embodiment of the infusion cartridge of FIG. 6 coupled to a drive mechanism embodiment.

DETAILED DESCRIPTION

Figure 1:
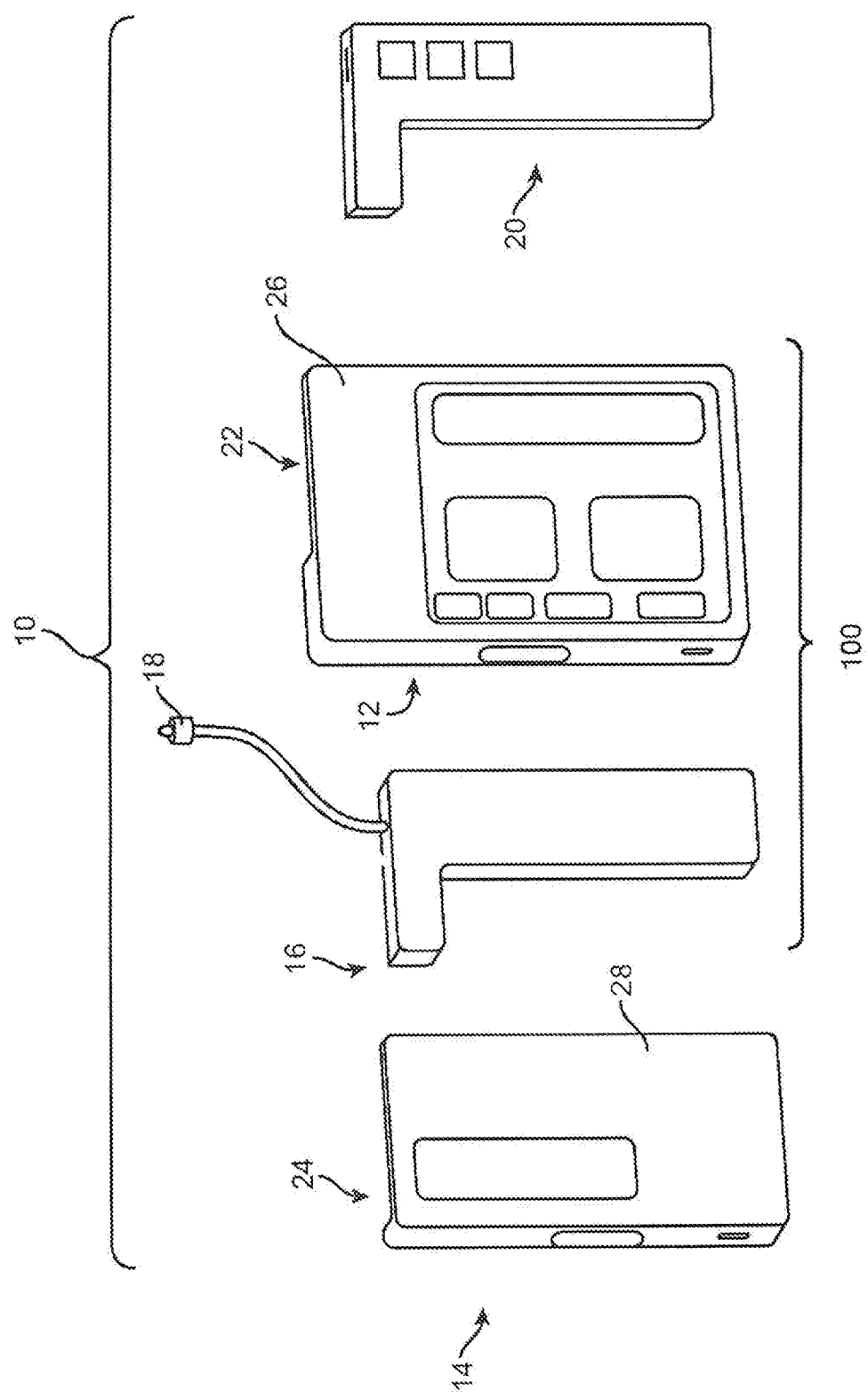
FIG. 1 depicts an embodiment of an interchangeable pump assembly.

Disclosed herein are methods and devices for detecting the capacity of a drug delivery reservoir, or a volume of medicine disposed in the drug delivery reservoir, and for setting therapeutic parameters of an infusion device such as a portable or ambulatory infusion pump. Some infusion device, system, and method embodiments discussed herein may account for a wide range of variables in determining an amount of medicament, e.g., insulin, to be infused into a patient over a given period of time. Further, some embodiments discussed herein may allow for refined regulation of the amount of medicament delivered as well as the time during which the medicament is delivered. Some embodiments may include advances in the internal components and the control circuitry, as well as improvements in a user interface. The advances may allow for an accurate regulation of blood glucose levels. Although embodiments described herein may be discussed in the context of the controlled delivery of insulin, delivery of other medicaments, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

With regard to one particular indication, maintaining appropriate blood glucose homeostasis is an important factor for promoting the length and quality of life of a diabetic patient. Different types of pumps provide a user of a pump with various advantages, though some of them may be mutually exclusive. For example, a portable pump device having a large output display can be easier to read and use when compared to a pump device with a smaller output display. However, those pumps may also have a housing that is generally larger and may require a greater power usage. Large and bulky ambulatory pump devices can be uncomfortable or unwieldy, contributing to problems with user compliance. For example, a user may be less likely to wear a larger pump device while sleeping, or when involved in certain activities. Smaller and more discreet pump systems can be more easily worn at night; however, they may not provide features that some patients may prefer for safety and convenience.

Some embodiments discussed herein may include an interchangeable pump assembly that may provide a user with the flexibility and convenience to alternate between pump devices having various features and advantages at any given moment during a single treatment protocol. In some cases, a single insulin cartridge may be switched between pump devices such as a smaller more discreet pumping device having fewer features and a larger pumping device having more features during a treatment with a single cartridge without compromising the sterility and thus wasting the cartridge.

It should be noted that labels associated with operations described below do not represent an order in a sequence; rather they are used only to uniquely identify each operation. The words, "loaded", "written", and "programmed" are used interchangeably when they refer to a processor or a memory device. The terms "pump" and "infusion pump" may be used interchangeably. The phrases "collapsible fluid reservoir" and "drug delivery reservoir" may be used interchangeably. The phrases "infusion cartridge" and "fluid reservoir cartridge" may be used interchangeably in this document. Also the phrases "sensor reading" and "sensor data" may be used interchangeably. Furthermore, as used herein, the term "fluid" shall mean a gas or a liquid, also the terms "fill" and "filling" shall mean increasing the amount of a fluid 84 in a collapsible fluid reservoir by some percentage of the total volume of the container up to 100%.

FIG. 1 depicts an embodiment of an interchangeable ambulatory infusion pump assembly 10 that may be used in pump embodiments configured to deliver a fluid or fluids from one or more reservoirs, which may be in fluid communication with a delivery mechanism thereof. The infusion pump assembly 10 may include an infusion pump 12, a second infusion pump 14, an infusion cartridge 16 having an infusion set connector 18, and optionally a glucose meter 20. The infusion cartridge 16 or the glucose meter 20 may be functionally and interchangeably inserted in a first receiving slot 22 located in the infusion pump 12 and a second receiving slot 24 located in the second infusion pump 14. The infusion pump 12 may have a housing 26 that may be generally larger than a second housing 28 of the second infusion pump 14. Similarly, the infusion pump 12 may generally include more operating features than the second infusion pump 14. Some or all of the suitable features, dimensions, materials, and methods of use of the infusion pump assembly 10 may be used or incorporated into any other infusion system, or components thereof, discussed herein. The interchangeability of infusion cartridge embodiments herein may be discussed in the context of transferring an infusion cartridge from the infusion pump 12 to the second infusion pump 14, having features different from those of the infusion pump 12. However, all of the interchangeability features and methods associated with this type of transfer may also be applied to the transfer of an infusion cartridge from the infusion pump 12 to a second infusion pump 14 having the same features as the infusion pump 12.

Figure 2:
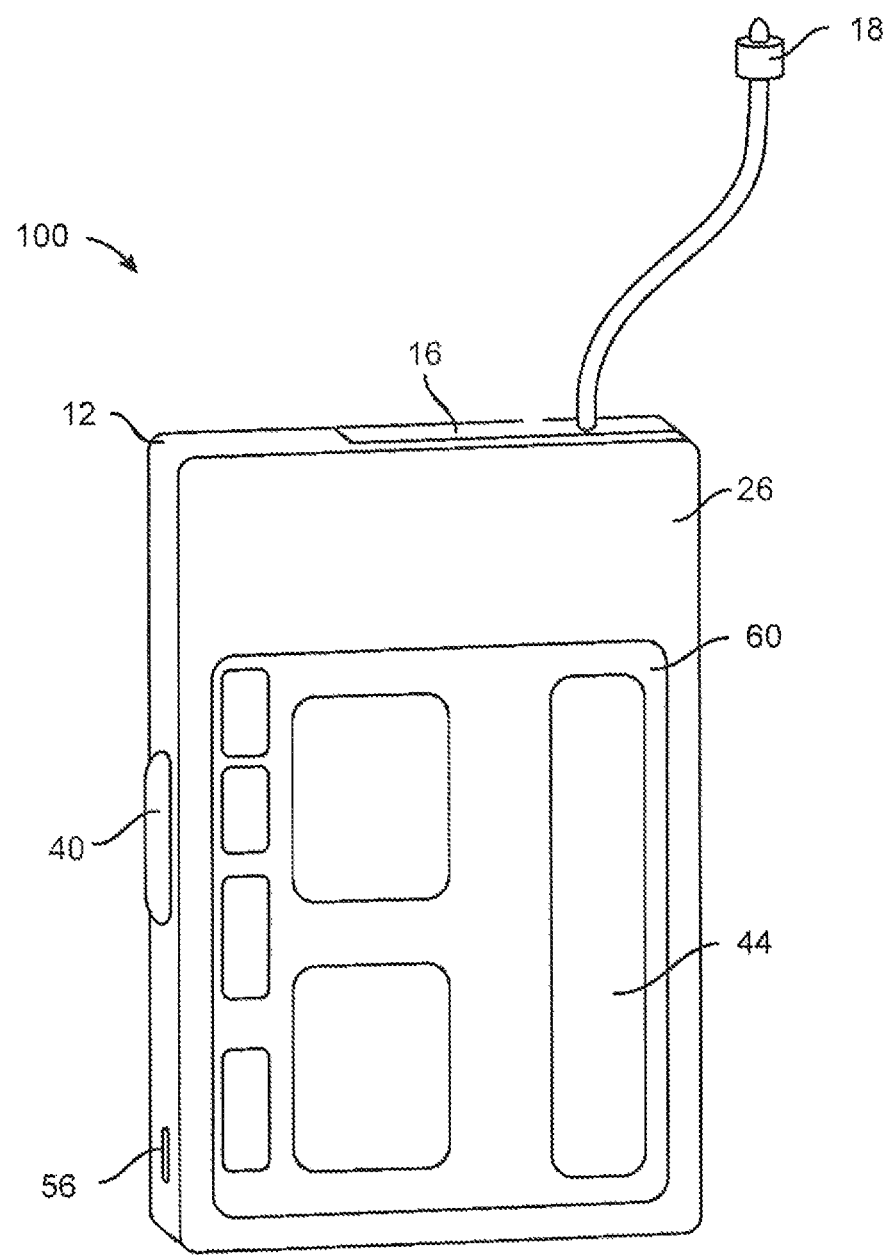
FIG. 2 depicts an embodiment of an infusion pump having an infusion cartridge embodiment coupled thereto.

FIG. 2 illustrates an embodiment of an ambulatory infusion pump system 100 which includes the infusion pump 12 and the infusion cartridge 16. The housing 26 of the infusion pump 12 can be of any suitable shape and size. For instance, the housing 26 may be extended and tubular, or in the shape of a square, rectangle, circle, cylinder, or the like. The housing 26 may be dimensioned so as to be comfortably associated with a user, and/or hidden from view, for instance, within the clothes of a user. In some embodiments, the housing 26 of the infusion pump 12 may have a width of about 2 inches to about 5 inches, a height of about 1 inch to about 3 inches and a thickness of about 0.25 inch to about 0.75 inch; more specifically, the housing 26 may have a width of about 2.5 inches to about 3.5 inches, a height of about 1.5 inches to about 2.5 inches and a thickness of about 0.4 inches to about 0.8 inches. The materials of the housing 26 may vary as well. In some embodiments, the housing of the infusion pump 12 may be a watertight, metal housing that may be taken apart for repairs.

The infusion pump 12 can include a user interface such as a graphic user interface (GUI) 60. The GUI 60 may include an output/display 44. The output/display 44 may vary as it may be useful for a particular application. The type of visual output/display may include LCD displays, LED displays, plasma displays and OLED displays. The output/display may also be an interactive or touch sensitive screen having an input device, such as a touch screen including a capacitive screen or a resistive screen. In some embodiments, the output/display 44 of the full infusion pump 12 may be an OLED screen and the input may be a capacitive touch screen. The infusion pump 12 may additionally include a keyboard or another input device 40 known in the art for data entry, which may be separate from the display. The output/display 44 of the infusion pump 12 may also include a capability to operatively couple to a secondary display device such as a laptop computer or a mobile communication device, such as a smartphone or personal digital assistant (PDA).

Figure 3:
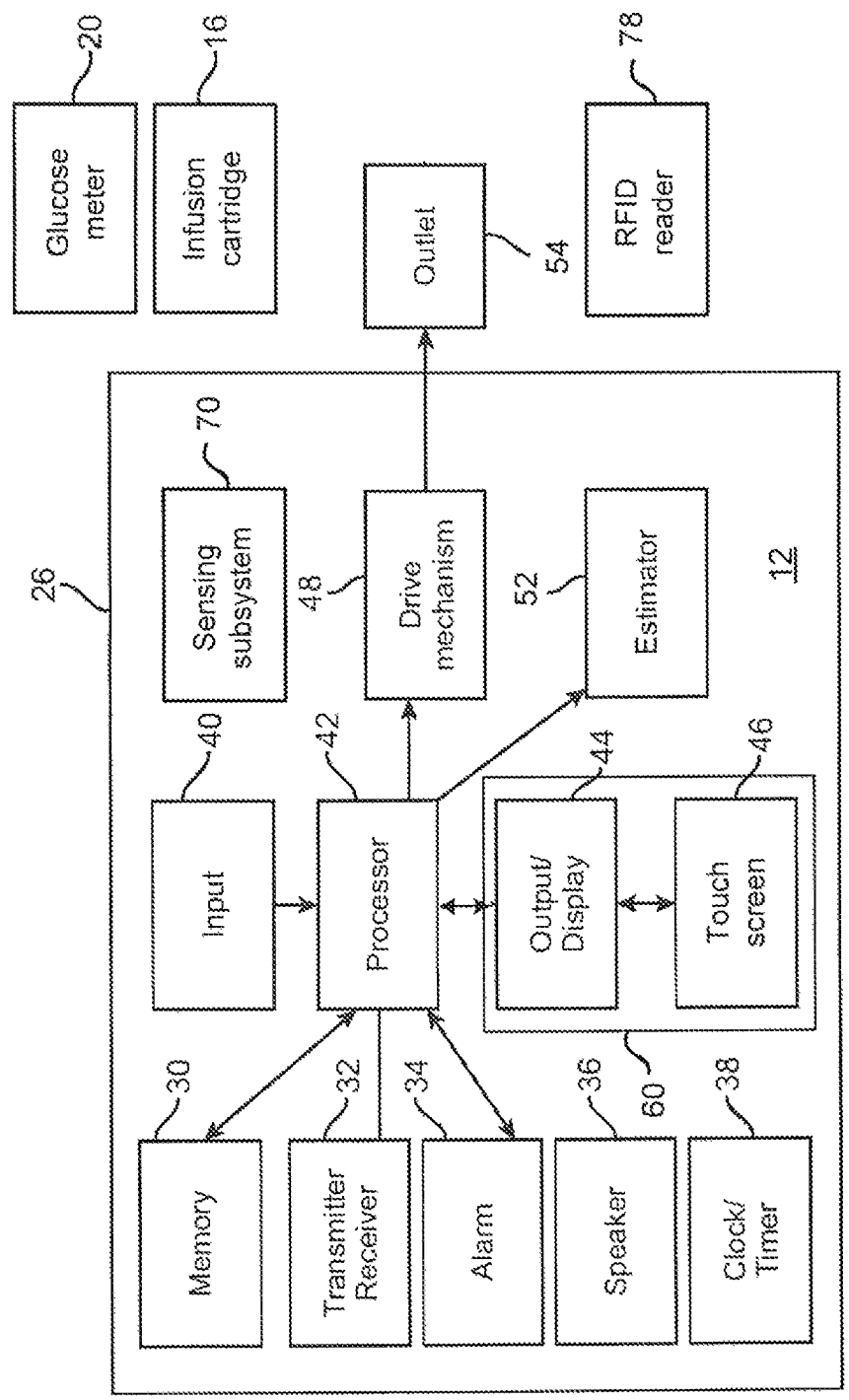
FIG. 3 depicts a block diagram representing an example of some elements of the infusion pump of FIG. 2.

The infusion pump 12 may have wired or wireless communication capability for the sending and receiving of data as is known in the art. The wireless capability may be used for a variety of purposes, including updating of any software or firmware for the processor of the device. The wireless communication capability may vary including, e.g., a transmitter and/or receiver, radiofrequency (RF) transceiver, WIFI connection, infrared or Bluetooth® communication device. The wired communication capability may also vary including, e.g., USB or SD port or flash drive port. In some embodiments, the infusion pump 12 may have a transmitter/receiver 32, such as a radiofrequency (RF) transceiver, as shown in FIG. 3 that may allow the infusion pumps to communicate with one another and may be used interchangeably without loss of data or information during an infusion protocol with an infusion cartridge 16. The infusion pump 12 may also act as a PDA or a controller to wirelessly control the second infusion pump 14. For such an embodiment, data may be transferred between the controller of the infusion pump 12 and the second infusion pump 14 by radio signal, optical transmission or any other suitable means. The first infusion pump 12 and the second infusion pump 14 may be used as stand-alone devices as well.

The infusion pump 12 may include a memory device 30. The memory device 30 may be any type of memory capable of storing data and communicating that data to one or more other components of the device, such as the processor. The memory device 30 may be one or more of a Flash memory, SRAM, ROM, DRAM, RAM, EPROM and dynamic storage. For instance, the memory device 30 may be coupled to the processor and configured to receive and store input data and/or store one or more template or generated delivery patterns. For example, the memory device 30 may be configured to store one or more personalized (e.g., user defined) delivery profiles, such as a profile based on a user's selection and/or grouping of various input factors or input data. The user input data may include one or more of blood glucose levels, a stress level, a physiological condition, complexity of a meal to be ingested, and an activity level. The user input data may include past generated delivery profiles; recommended delivery profiles; one or more traditional delivery profiles, e.g., square wave, dual square wave, basal rate and bolus profiles; and/or the like. In some embodiments, the memory device 30 of the full-featured infusion pump device 12 may be up to about 10 GB, more specifically, up to about 3 GB, even more specifically, about 1 MB to about 200 MB. In some embodiments, the memory device 30 of the full-featured infusion pump device 12 may be up to about 3 GB, more specifically, up to about 500 MB, and even more specifically, about 200 kB to about 200 MB.

The infusion pump 12 may include a power charging mechanism, such as a USB port, induction charger, or the like. The power charging system may be used to charge a power storage cell such as a rechargeable battery of the infusion pump 12. Some embodiments may use a rechargeable battery such as a NiCad battery, LiPo battery or NiMH battery. In some embodiments, the power charging mechanism 56 of the infusion pump 12 depicted in FIG. 2 may be a USB port. As such, all data may be kept in the infusion pump 12 for quick and easy downloading of data to a computer, other infusion pump device, network etc. using the USB port. The USB port 56 of the infusion pump 12 may also provide the infusion pump 12 with power charging. In some instances, the power charging mechanism of the infusion pump 12 may be an induction-charging device. In some cases, an advantage of having interchangeable infusion pump devices may be that while one infusion pump device is being used for infusion, the other infusion pump device can be charging.

The infusion pump 12 may also include programming to allow a processor to set therapeutic parameters and control the overall operation of the infusion pump 12. The therapeutic parameters may include a basal rate range, a bolus volume range, a max bolus volume range, and insulin sensitivity. The processor may include one or more infusion cartridge 16 sensing functionalities, which may allow the processor to receive data from various sources. The processor may collate data, parse the same, calculate a volume of a fluid disposed in the drug delivery reservoir or detect the reservoir capacity of the infusion cartridge 16 and may set therapeutic parameters for an infusion cycle. For example, the processor may receive input data from one or more pressure sensors which may be used for setting therapeutic parameters.

FIG. 3 illustrates a block diagram of some of the features that may be incorporated within the housing 26 of the infusion pump 12. The infusion pump 12 can include the memory device 30, the transmitter/receiver 32, an alarm 34, a speaker 36, a clock/timer 38, the input device 40, the processor 42, the user interface that may be GUI 60 having a touch sensitive screen 46 with input capability, a drive mechanism 48, and an estimator device 52. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump device 12. The GUI 60 may be configured for displaying a request for the user to input data and for receiving user input data in response to the request, and communicating that data to the memory.

The infusion pump 12 includes the processor 42 that functions to control the overall functions of the device. The processor 42 may communicate with and/or otherwise control the drive mechanism, output/display, memory, transmitter/receiver, and the like. The processor 42 of some embodiments of the infusion pump 12 may communicate with a processor of another device, for example, a radio-frequency identification (RFID) reader through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature, a continuous glucose monitor and other similar devices. The processor 42 may determine the capacity of the drug delivery reservoir and/or the volume of fluid disposed in the drug delivery reservoir and may set therapeutic parameters based on its determination.

As discussed above the housing 26 of the infusion pump 12 may be functionally associated with an interchangeable and a removable glucose meter 20 and/or infusion cartridge 16. The infusion cartridge 16 may have an outlet port 54 that may be connected to an infusion set (not shown) via an infusion set connector 18 (see FIG. 5).

The processor 42 may also include additional programming to allow the processor 42 to learn user preferences and/or user characteristics and/or user history data to, for example, implement changes in use, suggestions based on detected trends, such as, weight gain or loss, and may include programming that allows the device to generate reports, such as reports based upon user history, compliance, trending, and/or other such data. Additionally, infusion pump embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pumps, including a high power processor and a low power processor used to maintain programming and pumping functions in low power mode, in order to save battery life.

Figure 4:
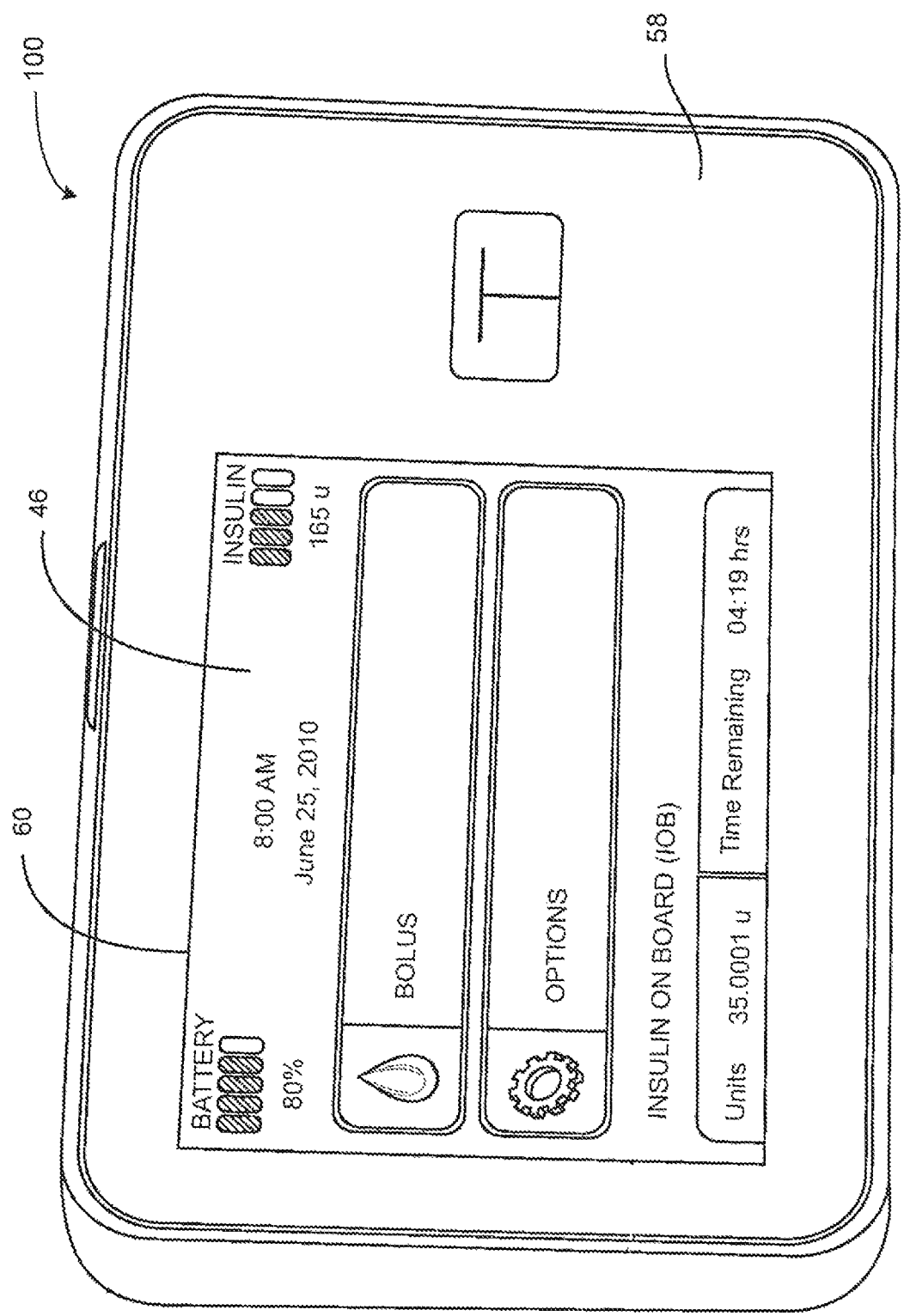
FIG. 4 depicts a perspective view of the infusion pump embodiment of FIG. 2 which can includes a graphic user interface with touch screen capability.

Referring to FIG. 4, a front view of the infusion pump 12 is shown. The infusion pump 12 may include a user-friendly GUI 60 on a front surface 58 of the infusion pump 12. The GUI 60 may include the touch sensitive screen 46 that may be configured to display a variety of screens used for displaying data, facilitating data entry by a patient, providing visual tutorials, as well as other interface features that may be useful to the patient operating the infusion pump 12.

Figure 5:
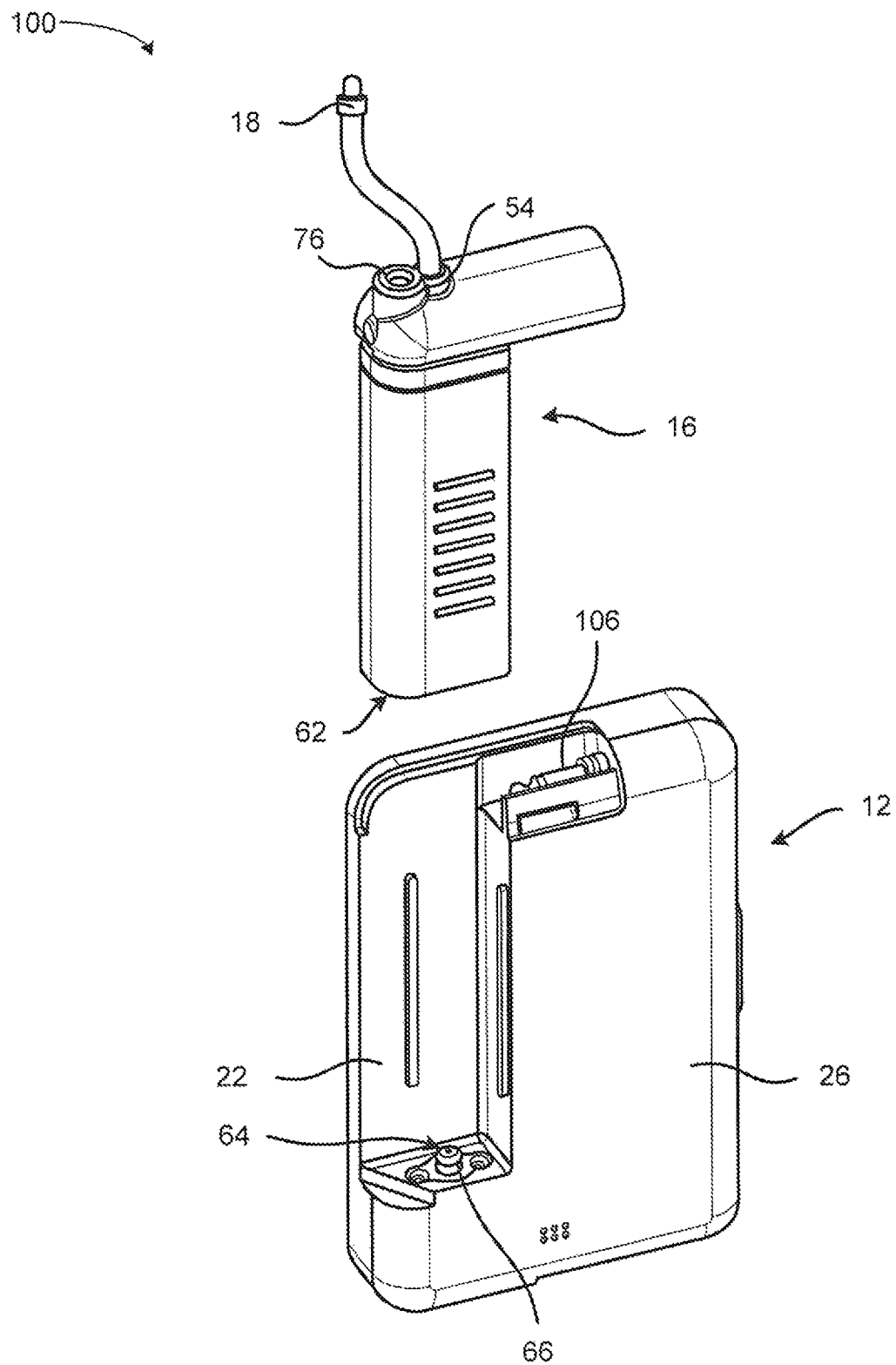
FIG. 5 is an exploded view of the infusion cartridge and infusion pump embodiment of FIG. 2 with the infusion cartridge removed from the infusion pump.

FIG. 5 depicts the infusion pump system 100 with the infusion cartridge 16 detached from the infusion pump 12. The infusion pump 12 may include an attachment mechanism 64 positioned within a first receiving slot 22 that corresponds to a receiving mechanism 62 at an end of the infusion cartridge 16. The attachment and receiving mechanisms may be configured to removably couple an interior volume of the cartridge with a volume of the pump that may be sealed from the surrounding environment with the coupling able to retain a fluid within the volumes even under significant pressure. The attachment may be so configured and suitable for producing a leak free detachable coupling that can withstand significant pressure. The infusion cartridge 16 may be removably attached to the housing 26 of the infusion pump 12 for fluid delivery. In this embodiment, the attachment mechanism 64 may include a pneumatic tap 66 having an O-ring or other sealing device. The corresponding receiving mechanism 62 positioned on an end of the infusion cartridge 16 may include a port through which the pneumatic tap 66 may be inserted. A reservoir fill port 76 may be disposed on a top portion of the infusion cartridge 16. In some cases, the desired fluid may be manually dispensed from the interior volume of a syringe or other device, through the reservoir fill port 76 into the interior volume of the infusion cartridge 16.

Figure 6:
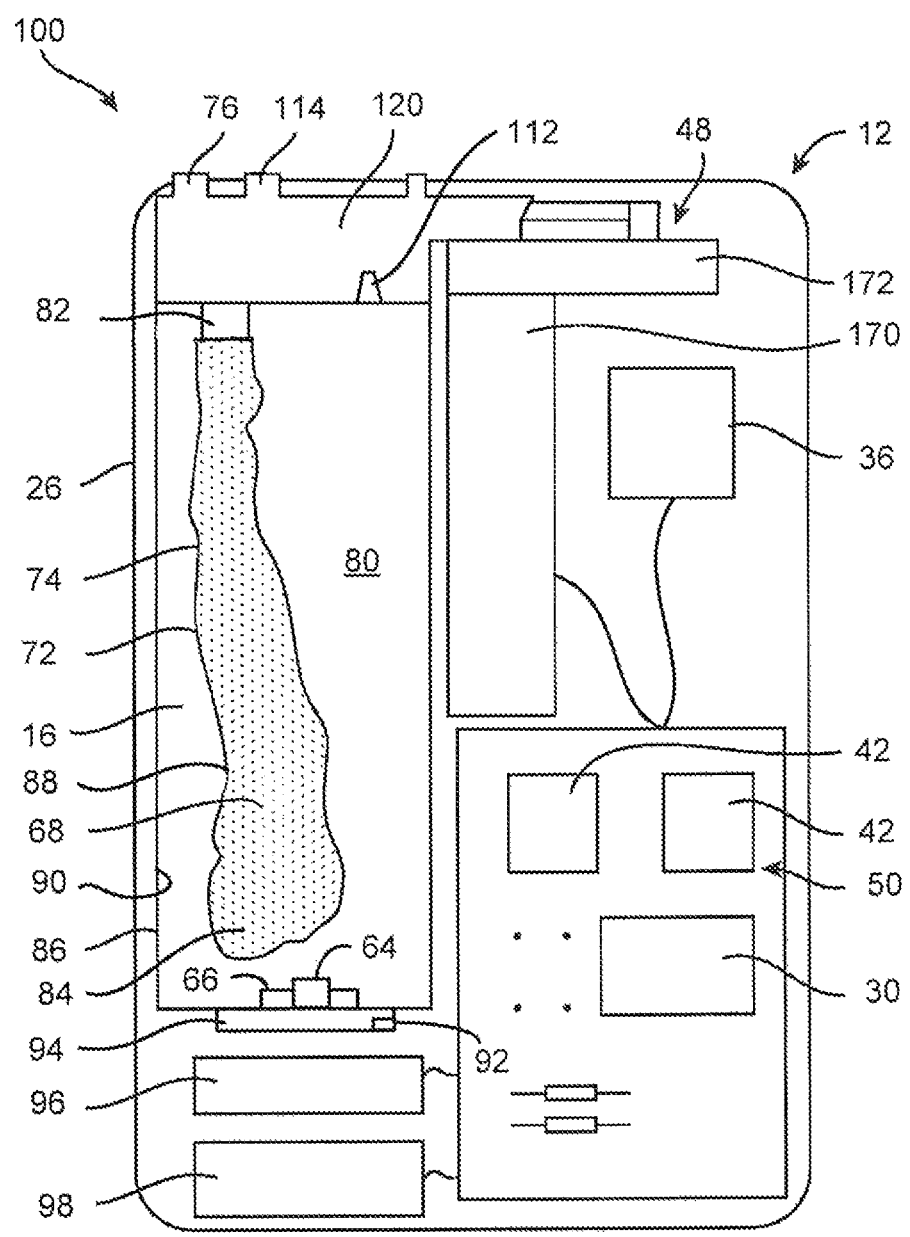
FIG. 6 is a schematic view partially cut away depicting some internal components of the infusion pump embodiment of FIG. 2 and the disposable infusion cartridge embodiment.

Referring to FIGS. 6-7, a collapsible fluid reservoir 68 of the infusion cartridge 16 may be bounded by or disposed within a flexible membrane or layer 72. The collapsible fluid reservoir 68 may include an interior volume 74 in fluid communication with a reservoir inlet port 108 of an axial bore 104 of a delivery mechanism 120. A top portion of the collapsible fluid reservoir 68 may be clamped or otherwise sealed to an extension or a boss 82 of the reservoir inlet port 108 that may extend into a first interior volume 80. In this configuration, the interior volume 74 of the collapsible fluid reservoir 68 may be isolated or sealed from the surrounding environment except for the reservoir inlet port 108, which may be in fluid communication with the axial bore 104 of the delivery mechanism 120.

A substantially rigid shell 86 may be disposed about the collapsible fluid reservoir 68 with a first interior volume 80 that may contain the collapsible fluid reservoir 68. The first interior volume 80 of the infusion cartridge 16 may be disposed between the outer surface 88 of the flexible membrane 72 and an interior surface 90 of the rigid shell 86. A vent inlet port 112 may be in fluid communication with the first interior volume 80 and the axial bore 104 of the delivery mechanism 120. The GUI 60 of FIG. 2 may be operatively coupled to a controller 50, which may include at least one processor 42, a memory device 30, and connective circuitry or other data conduits that couple the data generating and data managing components of the device. A power storage cell in the form of a battery 98 may be rechargeable and may also be disposed within the housing 26. Data generating or managing components of the device may include the processor(s) 42, the memory device 30, the GUI 60, a plurality of sensors including pressure sensors, temperature sensors, optical sensors, mechanical sensors and the like. Other components such as a vibratory motor 96, the speaker 36, the battery 98, and an electric motor 170 of the drive mechanism 48 may also be operatively coupled to the controller 50. Connective circuitry may include conductive wiring such as copper wiring, fiber optic conduits, RF conduits and the like.

With reference again to the infusion cartridge 16 generally shown in FIG. 6, the vent inlet port 112 may be disposed on the delivery mechanism 120 in fluid communication with the first interior volume 80 disposed between the outside surface 88 of the flexible material or membrane 72 of the collapsible fluid reservoir 68 and the inside surface 90 of the substantially rigid shell or case 86 of the infusion cartridge 16. The controller 50 may be coupled to at least one pressure sensor 92 which may be disposed in communication with a chamber 94 which may be in communication with the first interior volume 80 by means of attachment mechanism 64 and receiving mechanism 62. The controller 50 may be configured to generate signals to the drive mechanism 48 to displace the spool 106 of the delivery mechanism 120 based on a reading of the pressure sensor 92.

FIG. 7 depicts a portion of the infusion cartridge 16 including the delivery mechanism 120, as well as a portion of the drive mechanism 48 of the infusion pump 12. The delivery mechanism 120 may be configured to deliver fluid from the collapsible fluid reservoir 68 via a collapsible or variable volume element of the spool 106. For the embodiments discussed herein, the variable volume elements may include constrained variable volume elements that may be mechanically constrained to vary between a minimum volume and a maximum volume. The delivery mechanism 120 may include a delivery mechanism body 102, or housing, and an axial bore 104 disposed in the delivery mechanism body 102. The axial bore 104, may have a substantially round transverse cross section and includes a distal end 144, a proximal end 148 disposed towards the drive mechanism 48 of the infusion pump system 100, a reservoir inlet port 108, a fluid outlet port 114, a vent inlet port 112, and a vent outlet port 116. The spool 106, may also have a substantially round transverse cross section and may be slidingly disposed within the axial bore 104 to form a constrained variable volume 122 and a second sealed volume 154 with the axial bore 104.

The constrained variable volume 122 of the delivery mechanism 120 may be positionable to overlap the reservoir inlet port 108 independent of an overlap of the fluid outlet port 114. The constrained variable volume 122 may be formed between a first seal 140 around the spool 106, a second seal 142 around the spool 106, an outer surface of the spool body between the first and second seal 140 and 142 and an interior surface of the axial bore 104 between the first and second seal 140 and 142. The first and second seals 140 and 142 may be axially moveable relative to each other so as to decrease/increase a volume of the constrained variable volume 122, as when the first and second seals 140 and 142 move away from each other, decreasing the constrained variable volume 122, or when the first and second seals 140 and 142 may move closer together, increasing the variable volume 122.

The second seal 142 may be disposed on a proximal section 134 of the spool 106 and may move in conjunction with movement of the proximal section 134 of the spool 106. A proximal end of the spool 136 may be coupled to a ball portion 178 of a drive shaft 176 of the drive mechanism 48 of the infusion pump 12. The drive mechanism 48 includes a rack and pinion mechanism 174 actuated by an electric motor 170 through a gear box 172. As such, the second seal 142 may move or translate axially in step with axial translation of the spool 106 and drive shaft 176. The first seal 140, however, may be disposed on a distal section 128 of the spool 106, which may be axially displaceable with respect to the main section 190 of the spool 106. The distal section 128 of the spool 106 may be coupled to the main section of the spool by an axial extension 156 that may be mechanically captured by a cavity 158 in the main section 132 of the spool 106. This configuration may allow a predetermined amount of controlled axial movement between the distal section 128 of the spool and the main section 132 of the spool 106 and may translate the constrained variable volume 122 from the reservoir inlet port 108 to the fluid outlet port 114. This configuration may expand or contract the constrained variable volume 122 of the spool 106 by exerting translational axial force through a boundary section of the constrained variable volume 122.

For some embodiments, a volume of a "bucket" of fluid dispensed by a complete and full dispense cycle of the spool 106 may be approximately equal to the cross-sectional area of the axial bore 104 multiplied by the length of displacement of the captured axial extension of the spool for the distal section 128. The complete bucket of fluid may also be dispensed in smaller sub-volumes increments, as small as a resolution of the drive mechanism 48 allows. For some embodiments, a dispense volume or bucket defined by the constrained variable volume 122 of the delivery mechanism 120 may be divided into about 10 to about 100 sub-volumes to be delivered or dispensed. In some cases, the maximum axial displacement between the distal section 128 and main section of the spool 132 may be about 0.01 inch to about 0.04 inch, and more specifically, about 0.018 inch to about 0.022 inch.

For some embodiments, the axial bore 104 of the delivery mechanism may have a transverse dimension or diameter of about 0.04 inches to about 0.5 inches, and, more specifically, about 0.08 inches to about 0.15 inches. For some embodiments, the spool 106 may have a length of about 10 mm to about 40 mm, and, more specifically, about 15 mm to about 20 mm. The spool 106 and housing of the delivery mechanism 48 may be made from any suitable material or materials including polymers or plastics such as polycarbonate, PEEK, thermoplastics, cyclic olefin copolymer, and the like. In some cases, the seals disposed on the spool may have an outer transverse dimension or diameter that may be slightly larger than that of the spool 106. In some instances, the seals on the spool may have an axial thickness of about 0.01 inches to about 0.03 inches and may be made from materials such as butyl, silicone, polyurethanes or the like, having a shore hardness of about 65 A to about 75 A, and more specifically, about 70 A.

In some instances, a second volume 154 of the delivery mechanism 120 may be formed by the spool 106 and axial bore 104 of the delivery mechanism 48. The second volume 154 may be also be formed by a third seal 150 disposed around the spool 106 and a fourth seal 152 also disposed around the spool and axially separated from the third seal 150. In some instances, the axial separation between the third and fourth seals 150 and 152, forming the second volume 154, may be greater than the axial separation between the vent inlet port 112 and the vent outlet port 116 of the axial bore 104. The second volume 154 may also be formed by an outside surface of the spool 106 between the third and fourth seals 150 and 152 and an inside surface of the axial bore 104 between the third and fourth seals 150 and 152.

The second volume 154 may be axially displaceable with the movement of the spool 106, and may also be positionable by such axial displacement, in order to simultaneously overlap the second volume 154 with the vent inlet port 112 and the vent outlet port 116 of the axial bore 104. Such an overlap of both the vent inlet port 112 and the vent outlet port 116 may put these ports in fluid communication with each other and may allow an equilibration of pressure between the first interior volume 80 of the infusion cartridge 16 and the environment surrounding the vent outlet port 116 to vent the interior volume 80. In most cases, the vent outlet port 116 may be in communication with the atmosphere and air may pass from the environment surrounding the vent outlet port 116, through the second volume 154 of the axial bore 104 and into the first volume 80, to replace the fluid dispensed subsequent to the last vent cycle. When the vent inlet port 112 and vent outlet port 116 do not share a common volume formed by the spool and axial bore 104 of the delivery mechanism 120, they are typically isolated and no venting of the volume takes place.

In operation, the spool 106 and the volumes formed between the spool 106, the axial bore 104 and the circumferential seals 140, 142, 150 and 152 disposed on the spool of the delivery mechanism 120 are typically translated in a proximal and distal direction in order to move the volumes into and out of communication with the various ports of the axial bore 104. This axial movement in alternating proximal and distal directions of the spool 106, within the axial bore 104, may be used to put the various ports in fluid communication with translatable volumes of the delivery mechanism 120 and other ports of the mechanism. For reliable operation, it may be desirable, in some circumstances, for the spool 106 and the circumferential seals 140, 142, 150 and 152 disposed about the spool 106 to move smoothly within the axial bore 104 of the delivery mechanism 120, while maintaining a seal between an outside surface of the spool 106 and an inside surface of the axial bore 104. It may also be desirable for the circumferential seals 140, 142, 150 and 152 disposed on the spool 106 to move axially back and forth within the axial bore 104, while maintaining a seal and with a minimum of friction. Achieving these features of the spool 106 may be facilitated with the use of particular seal configurations, or gland configurations used to house the seals of the spool embodiments.

Figure 8A:
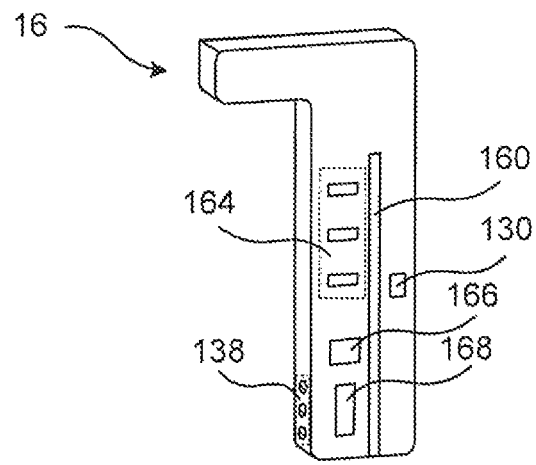
FIG. 8A is an elevation view of the infusion cartridge of FIG. 2 depicting locations for indicia.

Referring to FIG. 8A, an elevation view of the infusion cartridge 16 is shown depicting locations of indicia for capacity information. For some embodiments, the infusion cartridge 16, and any of the collapsible fluid reservoir cartridges discussed herein, may include one or more optically readable or detectable indicia, for example, a bar code type stripe 168 or a quick response code (QRC) label 166. In some embodiments the optically detectable indicium may be formed by up to three narrow blank light reflective stripes 164. The three reflective stripes 164 may represent three bits of data. Each of the light reflective stripes or the optically readable indicia may be configured to be detected by a corresponding optical reader device of the infusion pump system 100. In some cases such light reflective stripes may reflect a beam of light omnidirectionally or unidirectionally.

Figure 8B:
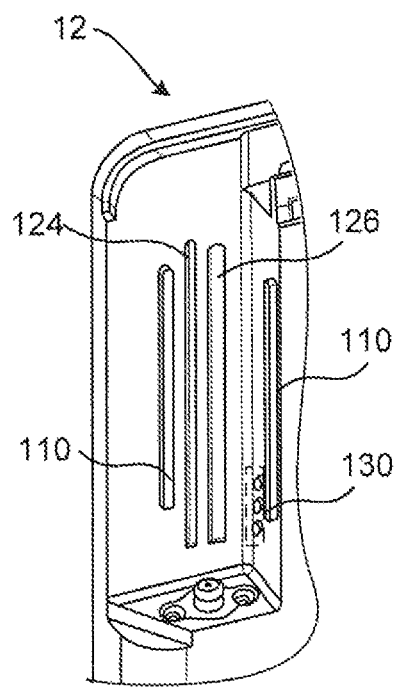
FIG. 8B is a partial exploded view of the infusion pump embodiment of FIG. 5 with the infusion cartridge removed depicting locations of various sensors.

FIG. 8B is a partial view of the infusion pump device 12 depicting locations of light sources and various readers. The optical reader device may be one of a bar code reader, a QRC reader, an array of photo sensors, or a combination of the above along with any other suitable sensors or detectors. In some instances infusion cartridge detection may rely on continuous readings of the three blank light reflective stripes. For some embodiments, a light source may illuminate one or more of the light reflecting stripes once the infusion cartridge is properly placed in the infusion pump device. A reflected beam of light from the light reflecting stripes may hit the photo sensor generating a digital value of 1 or other suitable indicium. A non-zero digital value may be used to indicate the presence of the infusion cartridge.

For some embodiments, the optical reader device may be in operative communication with the controller 50 or processor 42 of the pump. The encoder device may alternatively be an RFID tag or the like that may transmit data to a reader such as a data receiving processor, for example a RFID reader or the like. Such encoder device embodiments may include the ability to securely transmit and store data, via encryption, to prevent unauthorized access or tampering with such data. The identification of the infusion cartridge 16 and its content may be used by the controller 50 to set or to adjust certain dispense parameters or any other suitable parameters.

Figure 9:
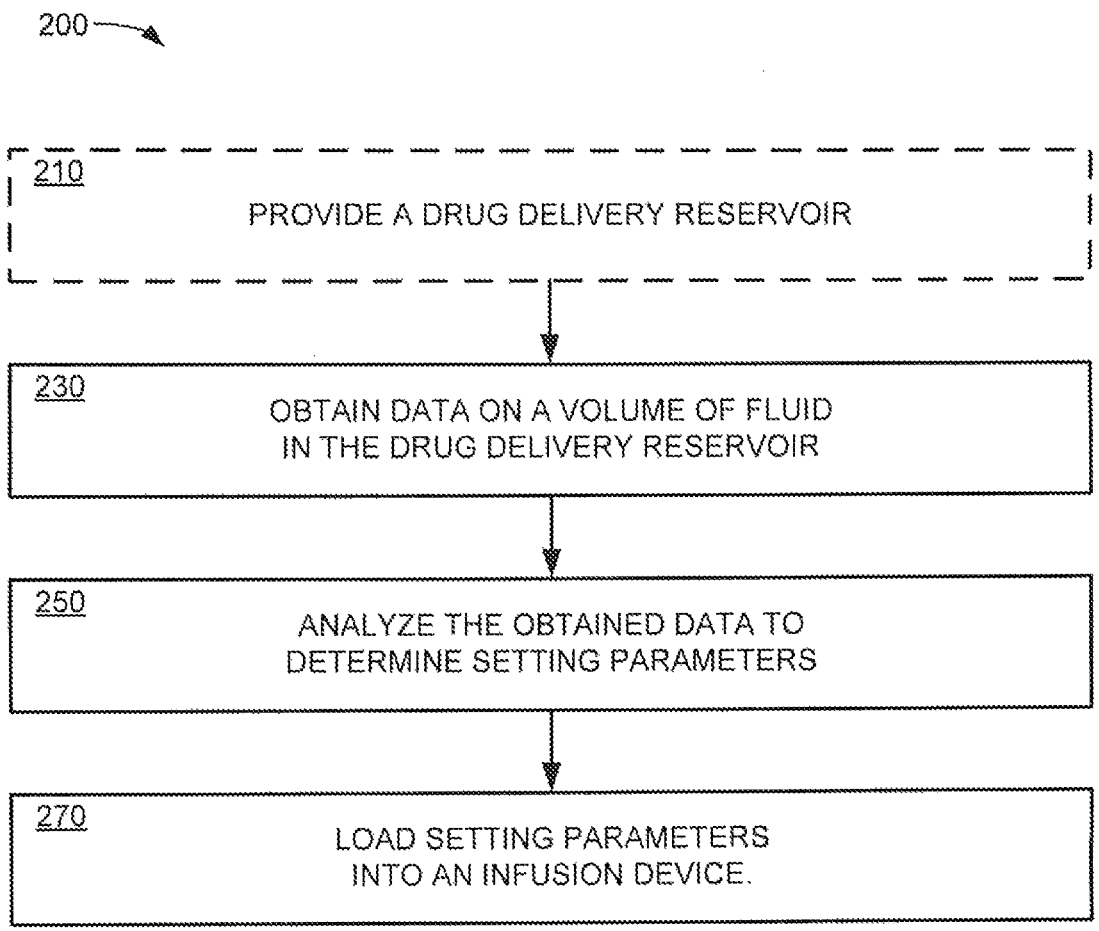
FIG. 9 is a flowchart of a method for detecting a capacity of a drug delivery reservoir of the infusion cartridge of FIG. 2 and for setting therapeutic parameters in the infusion pump according to an embodiment of the present disclosure.

Referring now to FIG. 9, a flowchart illustrates a method embodiment 200 of setting parameters of an infusion pump such as infusion pump 12. Method 200 may be used to determine the capacity of the collapsible fluid reservoir and/or the volume of medicine disposed in a collapsible fluid reservoir and to set delivery/therapeutic parameters of an infusion pump. Method 200 may start at operation 210, during which an infusion cartridge 16 containing the collapsible fluid reservoir 68 may be loaded into the infusion pump 12. In operation 230, data regarding the capacity of the collapsible fluid reservoir 68 and/or the volume of medicine disposed in the collapsible fluid reservoir 68 may be obtained by using various measurements and sensing techniques as discussed above. In operation 250, the obtained data may be analyzed by a processor 42 to determine therapeutic parameter settings to be loaded into a memory of an infusion pump 12 for access by a processor. In operation 270, the therapeutic parameter setting is loaded into the memory device for access by the processor.

Some of the method embodiments described herein may detect/determine the capacity of the reservoir 68 of the infusion cartridge 16. For some embodiments, the collapsible fluid reservoir 68 may have a volume of about 200 units, 300 units, and 500 units. Based on the detected capacity of the infusion cartridge 16, therapeutic parameter of the infusion pump 12 may be set. For example, the basal rate range, the bolus volume, and/or the max bolus volume range may be set lower for infusion cartridges with a smaller volume than for infusion cartridges with a larger volume. Furthermore, patients with high insulin sensitivity (where insulin sensitivity is defined as, units of insulin per mg/dl of blood glucose change) may be treated using a small capacity insulin cartridge.

Figure 10:
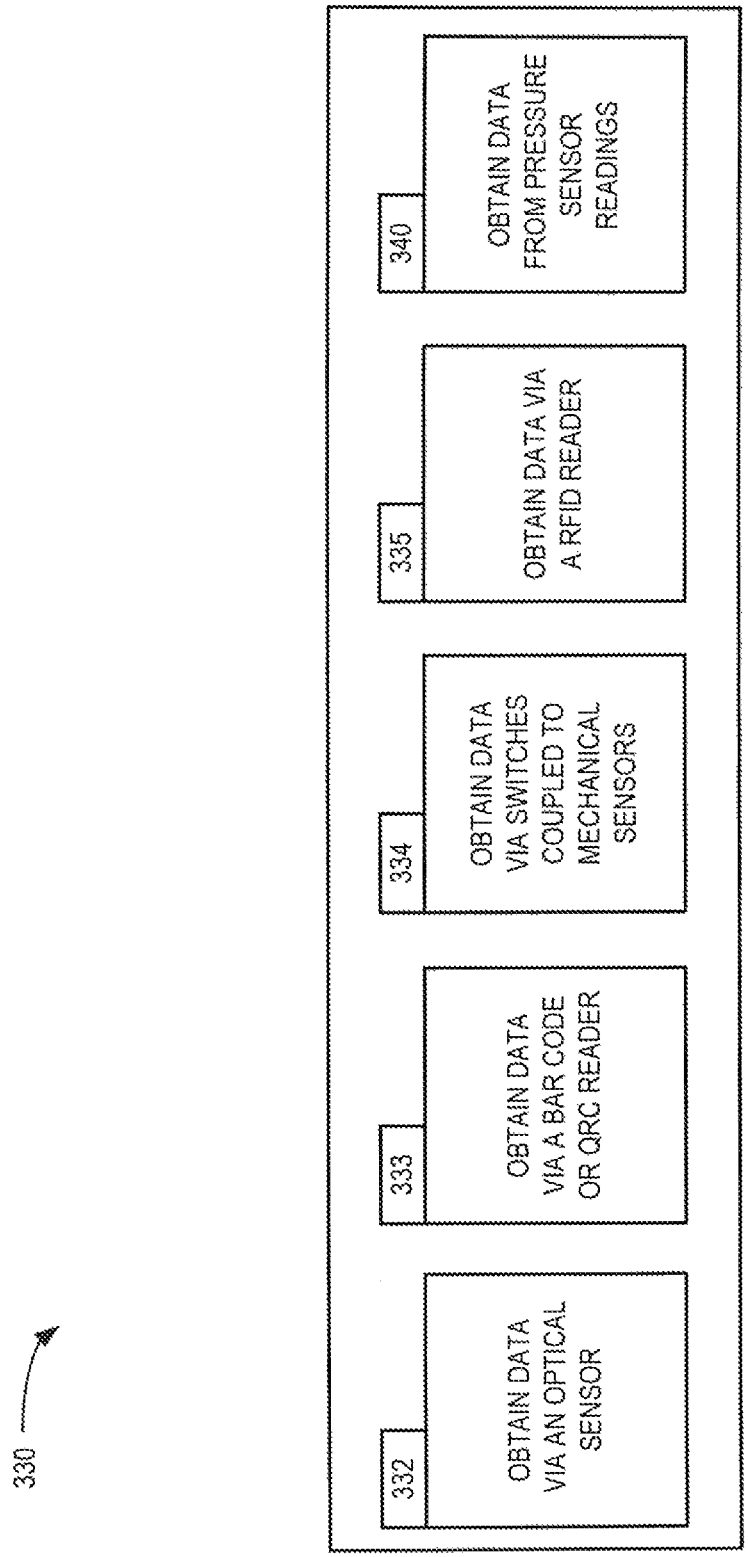
FIG. 10 is a flowchart of a method embodiment for obtaining data regarding the capacity of the drug delivery reservoir of FIG. 2.

FIG. 10 is a flowchart of a method embodiment 330 which depicts various measurements and sensing techniques employed for obtaining sensor data (volume data or capacity data) on the volume of fluid stored in the collapsible fluid reservoir 68, or a fluid capacity of the infusion cartridge 16 that may be loaded into the infusion pump 12. In operation 332, capacity data encoded in an optical code may be obtained by reading the optical code represented by reflected light using one or more optical sensors 126 as discussed above to obtain capacity data or detect the infusion cartridge 16. In some cases in addition to obtaining capacity data, a continuous monitoring of the presence of the light reflective stripes 164 may allow the processor 42 to determine whether the infusion cartridge 16 is present in the receiving slots or it has been removed or is inadvertently disconnected.

A method for detecting presence of an infusion cartridge in an infusion device can include illuminating the light reflective stripes 164 on the infusion cartridge 68, detecting reflected light from the reflecting stripes 68, determining whether data represented by the reflected light has a predetermined value and generating an audible warning signal indicating absence of a cartridge when data represented by the reflected light differs from the predetermined value.

In operation 333, capacity data may be obtained by using a bar code reader to read a bar code strip or a QRC label on the infusion cartridge. In operation 334, capacity data may be obtained by decoding the positions of switches. The switches may be operated by mechanical sensors that may be registered with surface grooves or dimples on the cartridge. In some instances, a groove configuration may be used to indicate the fluid capacity of the infusion cartridge 16. In operation 335, capacity data may be obtained via a RFID reader. The RFID reader may read an RFID tag that may be affixed to the cartridge. The RFID tag may store data indicating the capacity of the collapsible fluid reservoir. The RFID reader may be an external or an internal device to the infusion pump device. In cases where the RFID reader is an external device, the RFID reader data may be wirelessly communicated with the infusion pump device.

In operation 340, data may be obtained by reading a pressure sensor disposed in the cartridge during consecutive pressure measuring cycles. Changes in the pressure sensor readings may be indicative of the volume of fluid disposed in the collapsible fluid reservoir. Data on the capacity of the collapsible fluid reservoir may also be obtained by using a backstroke volume ($V_{backstroke}$), which is indicative of the capacity of the collapsible fluid reservoir 68 if the measurements are taken when the system is known to be empty of fluid. An example of a $V_{backstroke}$ determination technology is disclosed in U.S. patent application Ser. No. 12/714,299 which is incorporated herein by reference in its entirety.

An additional method of determining the identity or size classification of an infusion pump fluid cartridge may include reading a resistance value of a resistor (not shown) that is embedded in the infusion cartridge 16 as is coupled to the processor 42 of the infusion pump 12. The processor 42 may measure a resistance value of the embedded resistor to determine the size of the infusion cartridge 16. For example, different resistor values may indicate infusion cartridges 16 with different sizes of collapsible fluid reservoirs 68. For example, a 10 Ohm embedded resistor may indicate an infusion cartridge 16 with a small size collapsible fluid reservoir 68 and a 20 Ohm embedded resistor may indicate an infusion cartridge 16 with a large size collapsible fluid reservoir 68.

Figure 11:
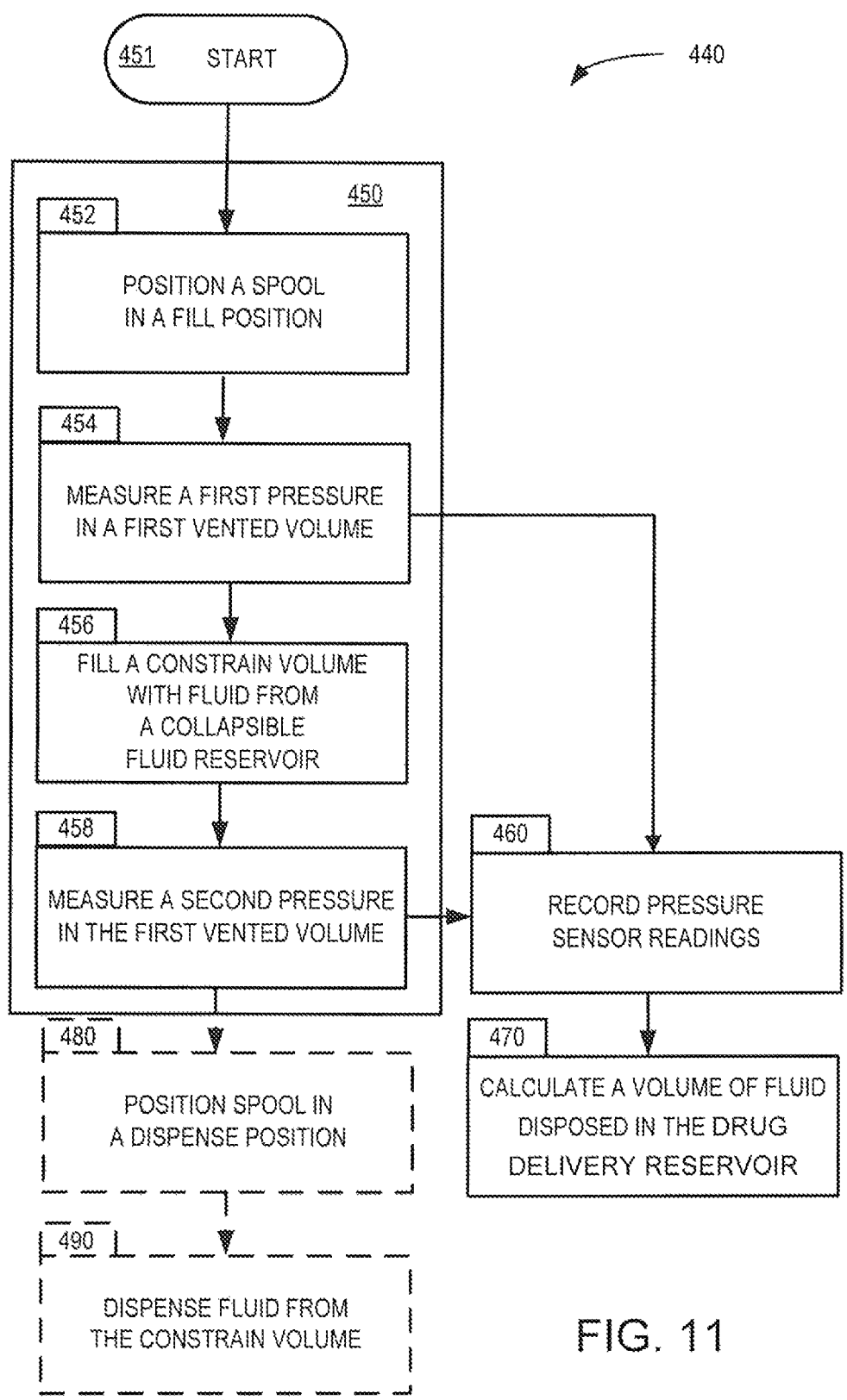
FIG. 11 is a flowchart of a method embodiment for obtaining data on a volume of a medicine disposed in the drug delivery reservoir of FIG. 6 by using a pressure metering technique embodiment.

FIG. 11 is a flowchart depicting a method embodiment 440 for using pressure sensor readings to obtain the volume of fluid disposed in the collapsible fluid reservoir 68. Function-block 450 shows the operations of the infusion pump 12 for executing a pressure metering cycle. Method embodiment 440 may start at operation 451. In operation 452, a spool of an infusion cartridge 16 may be positioned in a fill position. In operation 454, a first pressure measurement may be performed in the interior volume 80. In operation 456, the constrained variable volume 122 may be filled with a known amount of fluid removed from the collapsible fluid reservoir 68. In operation 458, a second pressure measurement may be performed in the interior volume 80. In operation 460, readings of the first and second pressure measurements may be recorded. In operation 470, the volume of fluid disposed in the collapsible fluid reservoir 68 may be calculated based on the first and second sensor readings. In operation 480, the spool of the infusion cartridge 16 may be positioned in a dispense position. In operation 490, fluid from the constrained variable volume 122 may be dispensed.

Figure 12:
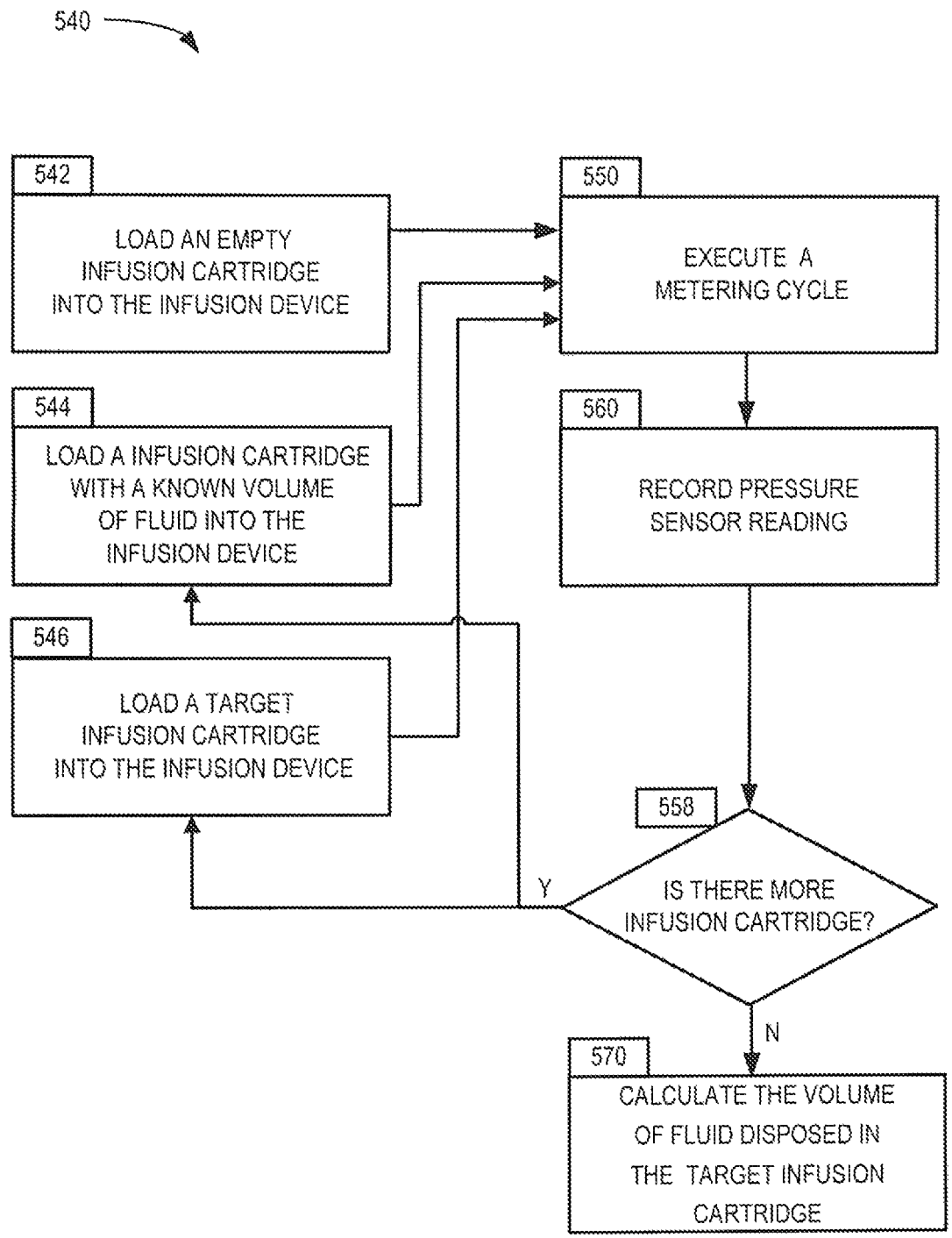
FIG. 12 is a flowchart of a method for obtaining data on a volume of a medicine disposed in the drug delivery reservoir of FIG. 6 by using a pressure metering technique embodiment.

FIG. 12 is a flowchart depicting a method embodiment 540 for using pressure sensor readings to obtain the volume of fluid disposed in the collapsible fluid reservoir. Method embodiment 540 may start at operation 542 during which an empty infusion cartridge may be loaded into the infusion pump 12. In operation 550, a first pressure metering cycle may be executed. In operation 560, following the pressure metering cycle, a first pressure sensor reading may be recorded. In operation 558, if it is determined that there is another infusion cartridge available, the method may loop back to operation 544 or 548 respectively; otherwise, the method may exit in operation 570. In operation 544, an infusion cartridge with a known volume of fluid may be loaded into the infusion pump 12 Operation 544 may be followed with a second execution of the pressure metering cycle 550 and the recording 560 of a second pressure sensor reading. In operation 546, a target infusion cartridge, i.e. an infusion cartridge that is intended to be used for a present therapy, may be loaded into the infusion device. Operation 548 may be followed with a third execution of the pressure metering cycle 550, and the recording 560 of a third pressure sensor reading. In operation 570, the volume of fluid disposed in the target infusion cartridge may be calculated based on the first, second and third pressure sensor readings.

Some of the above described method embodiments may detect/determine the capacity of the collapsible fluid reservoir 68 of the infusion cartridge 16. For some embodiments, the collapsible fluid reservoir 68 may have a volume of about 200 units, 300 units, and 500 units. Based on the detected capacity of the infusion cartridge 16, therapeutic parameter of the infusion pump 12 may be set. For example, the basal rate range, the bolus volume, and/or the max bolus volume range may be set lower for infusion cartridges with a smaller volume than for infusion cartridges with a larger volume. Furthermore, patients with high insulin sensitivity (where insulin sensitivity is defined as, units of insulin per mg/dl of blood glucose change) may be treated using a small capacity insulin cartridge.

Some of the above-described methods may determine the volume of medicine disposed in the drug delivery reservoir. Based on this volume, therapeutic parameters of the infusion pump may be precisely set or adjusted.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or data of these documents.

Modifications may be made to the foregoing embodiments without departing from the basic aspects of the technology. Although the technology may have been described in substantial detail with reference to one or more specific embodiments, changes may be made to the embodiments specifically disclosed in this application; yet, these modifications and improvements are within the scope and spirit of the technology. The technology illustratively described suitably herein, may be practiced in the absence of any element(s) not specifically disclosed herein. The terms and expressions which have been employed are used as terms of description and not of limitation and use of such terms and expressions do not exclude any equivalents of the features shown and described, or portions thereof, and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method for detecting a capacity of a fluid reservoir in an infusion cartridge and setting therapeutic parameters of a portable infusion pump with a processor of the portable infusion pump, comprising:
    obtaining from the infusion cartridge, with the processor, data relating to the fluid reservoir when the infusion cartridge is connected to the portable infusion pump;
    analyzing, with the processor, the obtained data relating to the fluid reservoir to determine the capacity of the fluid reservoir; and
    determining and setting with the processor, prior to delivering therapy using the infusion cartridge, one or more therapeutic parameters of the portable infusion pump based on the capacity of the fluid reservoir,
    wherein determining and setting one or more therapeutic parameters of the portable infusion pump based on the capacity of the fluid reservoir determines and sets one or more of the parameters at lower values for lower capacities and at higher values for higher capacities.

2. The method of claim 1, wherein setting one or more therapeutic parameters includes setting a basal rate range.

3. The method of claim 1, wherein setting one or more therapeutic parameters includes setting a bolus volume range.

4. The method of claim 1, wherein setting one or more therapeutic parameters includes setting a maximum bolus volume range.

5. The method of claim 1, wherein setting one or more therapeutic parameters includes setting an insulin sensitivity.

6. The method of claim 1, wherein obtaining data on the capacity of the fluid reservoir includes illuminating optical indicia on the infusion cartridge.

7. The method of claim 6, further including reading an optical code on the infusion cartridge that indicates the capacity of the fluid reservoir with an optical sensor.

8. The method of claim 7, wherein the optical code on the infusion cartridge is obtained from omnidirectionally reflecting stripes.

9. The method of claim 7, wherein the optical code on the infusion cartridge is obtained from unidirectionally reflecting stripes.

10. The method of claim 6, further including reading a bar code on the infusion cartridge that indicates the capacity of the fluid reservoir.

11. The method of claim 6, further including reading a quick response code on the infusion cartridge that indicates the capacity of the fluid reservoir.

12. The method of claim 1, wherein obtaining data on the capacity of the fluid reservoir includes sensing positions of a plurality of switches coupled to mechanical sensors of the portable infusion pump that are registered with surface grooves on the infusion cartridge indicating the capacity of the fluid reservoir.

13. The method of claim 1, wherein obtaining data on the capacity of the fluid reservoir includes reading a radio-frequency identification (RFID) tag affixed on the infusion cartridge, the RFID tag adapted to store data regarding the capacity of the fluid reservoir.

14. The method of claim 13, wherein reading the RFID tag is performed by an RFID reader, which is external to the portable infusion pump.

15. The method of claim 14, wherein the reading of the RFID reader is wirelessly communicated to the portable infusion pump.

16. The method of claim 13, wherein reading the RFID tag is performed by an RFID reader, which is secured to the portable infusion pump.

17. A method setting therapeutic parameters of a portable infusion pump having an infusion cartridge with a processor of the portable infusion pump, comprising:
    obtaining from the infusion cartridge, with the processor, a capacity of a fluid in the infusion cartridge when the infusion cartridge is connected to the portable infusion pump; and
    determining and setting with the processor, prior to delivering therapy using the infusion cartridge, one or more therapeutic parameters of the portable infusion pump based on the capacity of the fluid in the infusion cartridge,
    wherein determining and setting one or more therapeutic parameters of the portable infusion pump based on the capacity of the fluid in the infusion cartridge determines and sets one or more of the parameters at lower values for lower capacities and at higher values for higher capacities.

18. The method of claim 17, wherein setting one or more therapeutic parameters includes setting a basal rate range.

19. The method of claim 17, wherein setting one or more therapeutic parameters includes setting a bolus volume range.

20. The method of claim 17, wherein setting one or more therapeutic parameters includes setting a maximum bolus volume range.

21. The method of claim 17, wherein setting one or more therapeutic parameters includes setting an insulin sensitivity.

22. The method of claim 17, wherein obtaining a capacity of a fluid in the infusion cartridge includes illuminating optical indicia on the infusion cartridge.

23. The method of claim 22, further including reading an optical code on the infusion cartridge that indicates the capacity of the fluid with an optical sensor.

24. The method of claim 23, wherein the optical code on the infusion cartridge is obtained from omnidirectionally reflecting stripes.

25. The method of claim 23, wherein the optical code on the infusion cartridge is obtained from unidirectionally reflecting stripes.

26. The method of claim 22, further including reading a bar code on the infusion cartridge that indicates the capacity of the fluid.

27. The method of claim 22, further including reading a quick response code on the infusion cartridge that indicates the capacity of the fluid.

28. The method of claim 17, wherein obtaining a capacity of a fluid in the infusion cartridge includes sensing positions of a plurality of switches coupled to mechanical sensors of the portable infusion pump that are registered with surface grooves on the infusion cartridge indicating the capacity of the fluid.

29. The method of claim 17, wherein obtaining a capacity of a fluid in the infusion cartridge includes reading a radio-frequency identification (RFID) tag affixed on the infusion cartridge, the RFID tag adapted to store data regarding the capacity of the fluid.

30. The method of claim 29, wherein reading the RFID tag is performed by an RFID reader, which is external to the portable infusion pump.

31. The method of claim 30, wherein the reading of the RFID reader is wirelessly communicated to the portable infusion pump.

32. The method of claim 29, wherein reading of the RFID tag is performed by an RFID reader, which is secured to the portable infusion pump.

\* \* \* \* \*